United States Patent [19]

Möckli

[11] Patent Number: 4,547,579
[45] Date of Patent: Oct. 15, 1985

[54] SUBSTITUTED BENZOPYRAN COMPOUNDS

[75] Inventor: Peter Möckli, Basel, Switzerland

[73] Assignee: Ciba-Geigy Corporation, Ardsley, N.Y.

[21] Appl. No.: 430,416

[22] Filed: Sep. 30, 1982

Related U.S. Application Data

[62] Division of Ser. No. 949,939, Oct. 10, 1978.

[51] Int. Cl.⁴ .................................... C07D 311/92
[52] U.S. Cl. .................................... 549/280; 544/12; 544/133; 544/283; 544/287; 544/333; 544/353; 544/367; 546/47; 546/196; 546/269; 548/136; 548/138; 548/143; 548/144; 548/150; 548/159; 548/217; 548/326; 548/327; 548/518; 549/284; 549/285; 549/287; 549/289; 549/291; 549/293; 549/294; 549/389; 549/407; 549/399; 549/404; 549/405
[58] Field of Search .................. 548/159, 280, 389

[56] References Cited

U.S. PATENT DOCUMENTS

| | | | |
|---|---|---|---|
| 3,704,302 | 11/1972 | Enomoto et al. | 544/115 |
| 3,904,642 | 9/1975 | Mach et al. | 544/121 |
| 3,910,912 | 10/1975 | Scheuermann et al. | 544/64 |
| 3,920,704 | 11/1975 | Augart et al. | 544/80 |
| 3,954,743 | 5/1976 | Koch | 544/12 |
| 3,985,772 | 10/1976 | Scheuermann et al. | 544/376 |
| 4,002,619 | 1/1977 | Dengler et al. | 544/249 |
| 4,033,973 | 7/1977 | Schwander | 544/138 |
| 4,055,568 | 10/1977 | Patsch et al. | 544/209 |

OTHER PUBLICATIONS

Moeckli, "Chemical Abstracts", vol. 91, 1979, col. 91:40902f.
Moeckli, "Chemical Abstracts", vol. 93, 1980, col. 93:187730y.
Harnisch, "Chemical Abstracts", vol. 94, 1981, col. 94:176685g.
Harnisch, "Chemical Abstracts", vol. 95, 1981, col. 95:134383x.
Harnisch, "Chemical Abstracts", vol. 97, 1982, col. 97:40262w.
Claussen, "Chemical Abstracts", vol. 98, 1983, col. 98:225214w.

Primary Examiner—Glennon H. Hollrah
Assistant Examiner—James H. Turnipseed
Attorney, Agent, or Firm—Edward McC. Roberts; Kevin T. Mansfield

[57] ABSTRACT

There are described novel dyes of the formulae

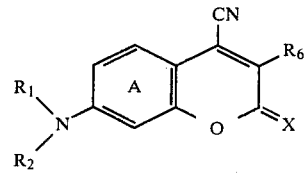

and

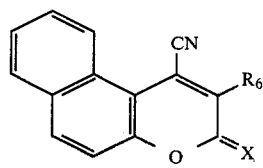

in which
R₁ and R₂ independently of one another are each hydrogen, unsubstituted or substituted alkyl, cycloalkyl, aralkyl or aryl, and R₁ and R₂ together with the nitrogen atom, and optionally with the inclusion of further hetero atoms, can also form a 5- to 7-membered heterocycle, or one of the radicals R₁ or R₂ can be linked with the carbon atoms, in the o-position with respect to the amino group, of the ring A to form a fused-on, saturated, unsubstituted or substituted 5- or 6- membered ring,
X is =NR₃, =NCOR₄,

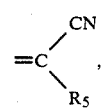

=NH or =O, wherein
R₃ is alkyl or unsubstituted or substituted phenyl,
R₄ is unsubstituted or substituted alkyl, aralkyl, aryl, vinyl, alkoxy, phenoxy or amino, and
R₅ is cyano, carbalkoxy, or unsubstituted or substituted carbonamide, and
R₆ is an electron-attracting radical,
processes for producing them, and their use for dyeing and printing synthetic and semi-synthetic fibres, such as polyamide and cellulose triacetate materials, especially however polyester materials.

2 Claims, No Drawings

SUBSTITUTED BENZOPYRAN COMPOUNDS

This is a divisional of application Ser. No. 949,939 filed on Oct. 10, 1978.

The present invention relates to novel dyes of the coumarin type which are free from water-solubilising groups and which contain in the 4-position of the coumarin structure a cyano group, to the production and use thereof for dyeing and printing synthetic and semi-synthetic fibres.

The novel dyes correspond to the general formulae

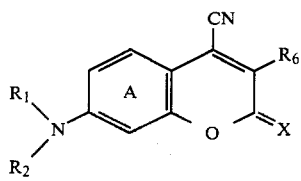 (I)

and

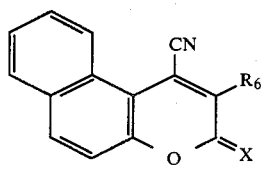 (II)

in which

R₁ and R₂ independently of one another are each hydrogen, unsubstituted or substituted alkyl, cycloalkyl, aralkyl or aryl, and R₁ and R₂ together with the nitrogen atom, and optionally with the inclusion of further hetero atoms, can also form a 5- to 7-membered heterocycle, or one of the radicals R₁ or R₂ can be linked with the carbon atom, in the o-position with respect to the amino group, of the ring A to form a fused-on, saturated, unsubstituted or substituted 5- or 6-membered ring, X is =NR₃, =NCOR₄,

particularly =NH and preferably =O, wherein
R₃ is alkyl or unsubstituted or substituted phenyl,
R₄ is unsubstituted or substituted alkyl, aralkyl, aryl, vinyl, alkoxy, phenoxy or amino, and
R₅ is carbalkoxy, or unsubstituted or substituted carbonamide, and preferably cyano, and
R₆ is an electron-attracting radical.

Electron-attracting radicals R₆ are in particular: the cyano group, the carbalkoxy group, an unsubstituted or substituted carbonamide group, or one of the following radicals:

(a)

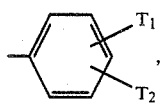

wherein R₁ is cyano or nitro, and T₂ is hydrogen, cyano, halogen, alkylsulfonyl, unsubstituted or substituted, especially alkyl-substituted, sulfonamide, or nitro:

(b)

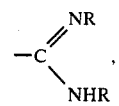

wherein R s independently of one another are each an unsubstituted or substituted alkyl, cycloalkyl, aralkyl or aryl group;

(c)

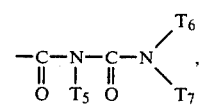

wherein T₅, T₆ and T₇ independently of one another are each hydrogen, an acyl group or an unsubstituted or substituted alkyl or phenyl group;

(d)

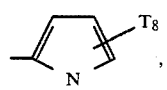

wherein T₈ is hydrogen, carbalkoxy, unsubstituted or substituted carbonamide, or cyano, and W is oxygen or sulfur;

(e)

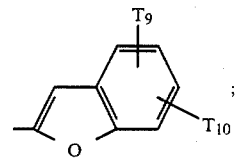

(f)

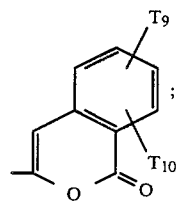

and (g)

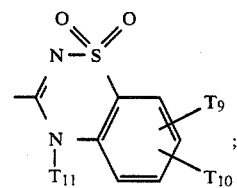

and in the formulae (e), (f) and (g), T₉ is hydrogen, alkyl, chlorine, bromine or alkoxy, T₁₀ is hydrogen or alkyl, and T₁₁ is acyl, or an unsubstituted or substituted alkyl or phenyl group, but preferably hydrogen;

(h) in particular an unsubstituted or substituted or annularly-linked pyrazole, imidazole, thiazole, oxazole, 1,2,4-triazole, 1,3,4-oxadiazole, 1,3,4-thiadiazole, quinoxalone, quinazolone, benzimidazole, benzoxazole, benzothiazole, pyridine, quinoline or pyrimidine ring, which is bound in the position adjacent to a ring-nitrogen atom to the coumarin ring, for example

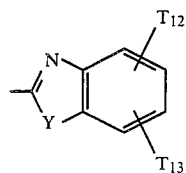

in which Y is oxygen, sulfur or the grouping

$T_{14}$ is hydrogen, alkyl or aralkyl, $T_{12}$ is hydrogen, alkyl, halogen or alkoxy, $T_{13}$ is hydrogen or alkyl, or $T_{12}$ and $T_{13}$ together can also form a further fused-on, unsubstituted or substituted aromatic ring; benzothiazole, benzoxazole or benzimidazole radicals, wherein the benzo radical can optionally be further substituted by Cl or $CH_3$, are preferred;

(i)

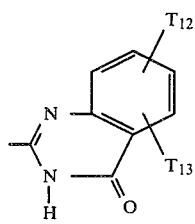

and (k)

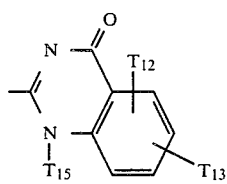

wherein $T_{12}$ and $T_{13}$ have the meanings given above, and $T_{15}$ is hydrogen, or unsubstituted or substituted alkyl or phenyl; and (l)

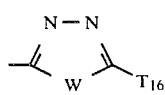

wherein W is oxygen or sulfur, and $T_{16}$ is unsubstituted or substituted alkyl, cycloalkyl, aralkyl, phenyl, pyridyl or the radicals —OZ, —SZ and

wherein Z is unsubstituted or substituted alkyl, cycloalkyl, aralkyl, aryl or heteroaryl, and $Z_1$ and $Z_2$ independently of one another are each hydrogen or unsubstituted or substituted alkyl, cycloalkyl, aralkyl or aryl, and $Z_1$ and $Z_2$ together with the nitrogen atom can form a heterocyclic ring.

The substituents R, T or Z as alkyl groups can be identical or different, straight-chain or branched-chain; they are in particular low-molecular alkyl groups having 1 to 7, particularly 1 to 4, carbon atoms, such as methyl, ethyl, propyl, isopropyl, tert-butyl, amyl, hexyl or heptyl, or alkyl groups having a longer chain, such as octyl, decyl or dodecyl. Possible substituents are for example: hydroxyl, low-molecular alkoxy or carbalkoxy, phenoxy, cyano, carbonamido, halogen, especially chlorine or bromine, and acetoxy. $R_1$ and $R_2$ are advantageously methyl or ethyl.

A cycloalkyl group denoted by R, T or Z is in particular the cyclohexyl or methylcyclohexyl group, and an aralkyl group is especially the benzyl, phenethyl or β-phenyl-β-hydroxyethyl group.

If $R_1$ and $R_2$, or $Z_1$ and $Z_2$, together with the nitrogen atom, and optionally with the inclusion of further hetero atoms such as O, S or N, form a 5- to 7-membered hetero ring, this is for example the piperidine, pyrrolidine, morpholine, piperazine or N-methyl-piperazine ring.

If $R_1$ or $R_2$ together with the nitrogen atom form a radical fused on in the ortho-position with respect to the nitrogen atom of the ring A, it is preferably one the following groupings:

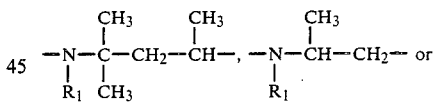

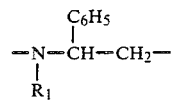

If R, T or Z is an aryl group, it is for example the naphthalene group or preferably the phenyl group.

Possible nonionic substituents on the aryl group, particularly on the phenyl group, and also on the benzo groups, are: one or more alkyl groups such as methyl, ethyl or isopropyl, alkoxy groups such as methoxy or ethoxy, acylamino groups such as acetylamino or benzoylamino, halogen atoms such as chlorine or bromine, hydroxyl, cyano, rhodan, amino, mono- and dialkylamino, phenylamino, N-phenyl-N-alkylamino, phenyl, phenoxy, nitro, acyl or acyloxy, such as acetyl or acetoxy. Methyl or ethyl are preferred.

The substituted carbonamide or sulfonamide groups preferably contain 1 to 10 carbon atoms, and are preferably N-methyl-, N,N-dimethyl-, N-ethyl-, N,N-diethyl-, N-benzyl- and N-phenylcarbonamide or -sulfonamide.

Dyes of the coumarin type are known and are described in numerous patent specifications. Common to all of them is that they contain in the 4-position of the coumarin structure a hydrogen atom or possibly a lower alkyl group.

These dyes have attained great commercial importance because by means of them it is possible to dye synthetic fibres in extremely brilliant fluorescent shades. Unfortunately, their range of shades is very limited, and extends almost exclusively to the greenish-yellow shades.

It has now been found that the hydrogen atom in the 4-position of the known coumarin dyes can be replaced in a simple manner by a cyano group. The novel dyes of the formulae I and II according to the invention are distinguished by a surprisingly intense deepening of the shades.

Thus, for example, the dye of the formula

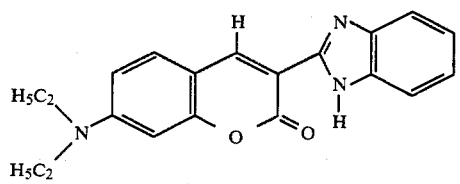

mentioned in the German Auslegeschrift No. 1,098,125 and the dye of the formula

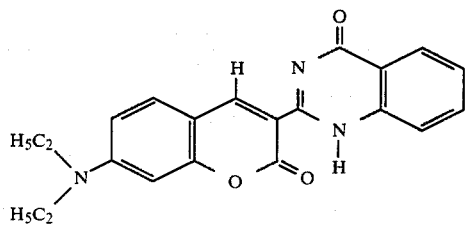

mentioned in the German Auslegeschrift No. 2,306,843 dye polyester fibres in brilliant greenish-yellow shades. The corresponding dyes according to the present invention which have a cyano group in the 4-position of the coumarin ring and which have the following formulae

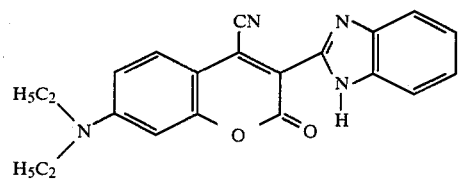

and

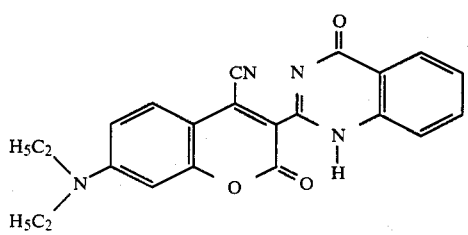

respectively, dye polyester in red shades, the former of these dyes giving an extraordinarily brilliant shade.

As a further example of the considerable bathochrome change of shade caused by the cyano group in the 4-position, there may be mentioned the red dye of the formula

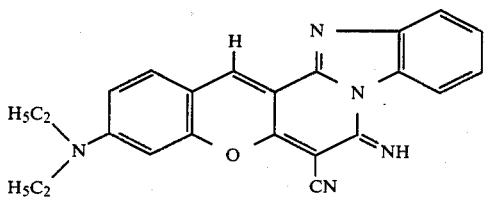

mentioned in the German Offenlegungsschrift No. 2,328,146. The corresponding dye according to the invention, which contains a cyano group and has the formula

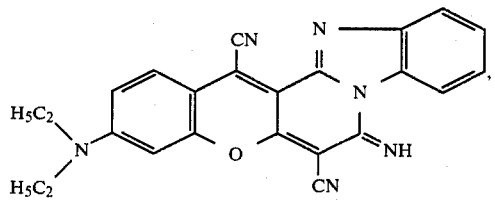

dyes polyester fibres in blue shades.

Of particular interest are those dyes of the formula I or II according to the invention, wherein $R_1$ and $R_2$ independently of one another are methyl, ethyl or phenyl, X is oxygen, and $R_6$ is an unsubstituted or substituted or annularly-linked pyrazole, imidazole, thiazole, oxazole, 1,2,4-triazole, 1,3,4-oxadiazole, 1,3,4-thiadiazole, quinoxalone, quinazolane, benzimidazole, benzoxazole, benzothiazole, pyridine, quinoline or pyrimidine ring, which is linked in a position adjacent to to a ring nitrogen atom with coumarin ring; and especially those dyes wherein $R_6$ is a benzothiazole, benzoxazole or benzimidazole group, or a 5-phenyl-1,3,4-thiadiazole group.

The novel dyes are obtained by reacting a compound of the formula

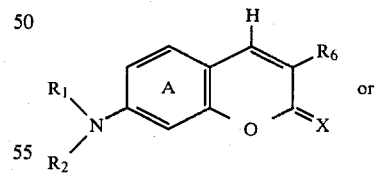 or

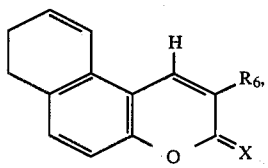

in which $R_1$, $R_2$, $R_6$ and X have the same meanings as under the formula I or II, in a polar solvent, with cyanide salts, and treating the reaction product either simultaneously or subsequently with oxidising agents.

Examples of polar solvents which may be mentioned are alcohols, but preferably dimethyl formamide. Using phase-transfer catalysis, however, the reaction can be performed also in a nonpolar solvent.

The addition product is advantageously not isolated before the oxidation treatment. The majority of customary commercial oxidising agents are suitable for the process, for example persulfates, dibenzoyl peroxide or chloranil, preferably however lead tetraacetate or nitric acid, and particularly bromine.

The treatment of the starting product with cyanide salts, advantageously water-soluble cyanide salts such as sodium, potassium or ammonium cyanide, is performed generally at temperatures between 0° and 120° C., preferably between 10° and 40° C.

Oxidation with bromine is carried out advantageously at temperatures between 0° and 80° C. The lower the temperature, the purer are in general the resulting dyes. It is advantageous to perform the oxidation at a temperature of between 5° and 10° C.

Suitable starting materials for producing the dyes according to the invention are coumarin compounds having a hydrogen atom in the 4-position of the coumarin ring, such as are described for example in the following patent specifications:

German Auslegeschrift No. 1,469,770;

German Offenlegungsschriften Nos. 1,619,567, 2,005,933, 2,301,738, 2,306,740, 2,306,843, 2,312,133, 2,319,230, 2,334,168, 2,430,980, 2,529,434 and 2,553,294.

Among the coumarin dyes of the following patent specifications, only those having no cationic charge are suitable for producing the dyes according to the invention: German Offenlegungsschriften Nos. 1,098,125, 2,126,811, 2,144,591, 2,226,211 and 2,234,207.

The novel dyes are suitable in some cases for producing organic lasers.

The novel dyes are suitable for dyeing or printing synthetic and semi-synthetic textile material, for example made from polyamides or triacetate, and particularly polyesters, and also for dyeing plastics in the melt. Those dyes of the formulae I and II which are distinguished by brilliance and fluorescence are suitable also for improving other less brilliant dyes.

Readily subliming dyes are also suitable for transfer printing on cellulose triacetate, polyacrylonitrile and especially polyester materials.

The dyeing of the stated fibre materials with the difficultly water-soluble dyes according to the invention is preferably performed from an aqueous dispersion. It is hence advantageous to finely divide the representatives, usable as disperse dyes, by grinding with textile auxiliaries, e.g. dispersing agents, and if possible with grinding auxiliaries. On subsequent drying there are obtained dye preparations comprising the textile auxiliary and the dye.

As advantageously usable dispersing agents of the nonionic group, there may be mentioned for example: addition products of 8 mols of ethylene oxide with 1 mol of p-tert.-octylphenol, of 15 or 6 mols of ethylene oxide with castor oil, of 20 mols of ethylene oxide with the alcohol $C_{16}H_{33}OH$, ethylene oxide addition products with di-[α-phenylethyl]-phenols, polyethylene oxide-tert.-dodecyl-thioethers, polyamide-polyglycol ethers, or addition products of 15 or 30 mols of ethylene oxide with 1 mol of $C_{12}H_{25}NH_2$ or $C_{18}H_{37}NH_2$.

Anionic dispersing agents which may be mentioned are: sulfuric acid esters of alcohols of the aliphatic series having 8 to 20 carbon atoms, of the ethylene oxide adducts of the corresponding fatty acid amides, or of alkylated phenols having 8 to 12 carbon atoms in the alkyl group; sulfonic acid esters with alkyl groups having 8 to 20 carbon atoms; sulfating products of unsaturated fats and oils; phosphoric acid esters with alkyl groups having 8 to 20 carbon atoms; fatty acid soaps, also alkyl aryl sulfonates, condensation products of formaldehyde with naphthalenesulfonic acid and lignin sulfonates.

Suitable cationic dispersing agents are quaternary ammonium compounds containing alkyl or aralkyl groups having 8 to 20 carbon atoms.

The dye preparations can contain, in addition to the dispersing agents, organic solvents, particularly organic solvents boiling above 100° C., which are preferably miscible with water, such as mono- and dialkyl glycol ethers, dioxane, dimethyl formamide or dimethyl acetamide, tetramethylene sulfone or dimethyl sulfoxide. Dye, dispersing agent and solvent can be advantageously ground together.

The dyeing of the polyester fibres with the difficultly water-soluble dyes, according to the invention, from an aqueous dispersion is performed by the processes customary for polyester materials. Polyesters of aromatic polycarboxylic acid with polyhydric alcohols are dyed preferably at temperatures of above 100° C. under pressure. The dyeing can however also be carried out at the boiling point of the dye bath in the presence of dye carriers, for example phenylphenols, polychlorobenzene compounds or similar auxiliaries; or it can be carried out by the thermosol process, that is, padding with subsequent aftertreatment at elevated temperature, for example thermofixing, at 180° to 210° C. Cellulose-2½-acetate fibres are preferably dyed at temperatures between 80° and 85° C., whilst cellulose triacetate fibres are advantageously dyed at the boiling point of the dye bath. The use of dye carriers is not necessary in the dyeing of cellulose-2½-acetate or polyamide fibres. Dyes according to the invention can be used also for printing the stated materials by customary methods.

The dyeings obtained by the present process can be subjected to an aftertreatment, for example by heating in an aqueous solution of an ion-free detergent.

Instead of by impregnation, the dyes mentioned can be applied according to the invention also by printing. For this purpose, there is used for example a printing ink containing, besides the auxiliaries customary in the printing industry, such as wetting and thickening agents, the finely dispersed dye.

The materials can be in the most varied stages of processing, such as threads, knitwear, fabrics, yarns or fibres.

By the present process are obtained full dyeings and printings, some having a fluorescent shade, which have good general fastness properties, for example fastness to light, thermofixing, sublimation, pleating, flue gases, cross-dyeing, dry-cleaning, ironing, rubbing, chlorine and wet processing, such as fastness to water, washing and perspiration.

Except where otherwise stated in the following Examples, the term 'parts' denotes parts by weight, percentages are given as percent by weight and the temperatures in degrees Centigrade. The Examples are intended to illustrate the invention without in any way limiting its scope.

EXAMPLE 1

87.5 g of the dye of the formula

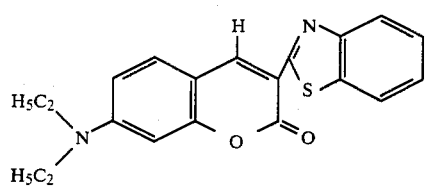

is suspended in 525 ml of dimethylformamide. To the suspension is then added at room temperature 82 ml of a 30% aqueous sodium cyanide solution, in the course of which the temperature rises to about 35°. Stirring is subsequently maintained for about 1 hour at 40°–45°, with the suspension gradually going almost completely into solution. The clear yellow solution is cooled to 8°–10°, and 14.8 ml of bromine is added dropwise within 2 hours. A brown, readily stirrable suspension is formed; it is further stirred for 2 hours at 10°, finally filtered, and the residue is washed with 131 ml of dimethyl formamide. In order to remove inorganic salts, the press cake is well stirred up in 2000 ml of hot water, filtered off with suction, and washed with water until free from salt. Drying at 80° in vacuo yields 83.5 g of the dye of the formula

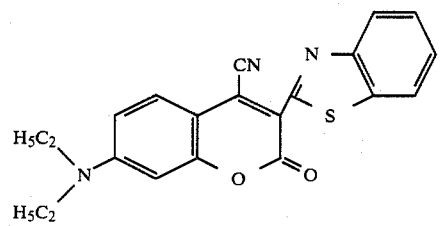

melting point: 243°.

The dye dyes polyester fibres, by the customary dyeing processes, in bluish-red fluorescent shades having good fastness properties.

The dye can be produced also by oxidation with nitric acid. In this case, 43.6 ml of nitric acid (96%), instead of 14.8 ml of bromine, is added dropwise to the ice-cooled dimethyl formamide solution. Stirring is continued overnight at room temperature, and there is then carefully added 92.5 g of sodium bicarbonate. The mixture is stirred for a further hour, then filtered, and the residue is boiled 3 times with 600 ml of isopropanol each time. It is subsequently washed thoroughly with water and dried; yield: 79.5 g.

EXAMPLE 2

3.5 g of the dye of the formua

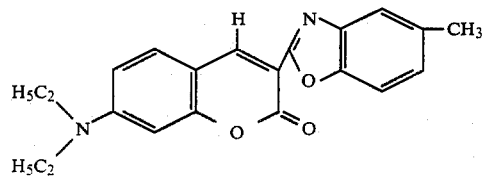

is introduced into 20 ml of dimethyl formamide; 1.5 ml of 30% aqueous sodium cyanide solution is added, and stirring is maintained for 30 minutes at room temperature. The solution is filtered, and to the filtrate is added 4.6 g of lead tetraacetate. There immediately forms a red suspension, which is stirred for 1 hour and then filtered; the suction-filter residue is washed firstly with a small amount of dimethyl formamide and then with water until free from salt, and is finally recrystallised from 300 ml of ethyl alcohol. The yield after drying is 1.5 g of a dark-red powder having needle-shaped particles and a melting point of 203°. The dye obtained corresponds to the formula

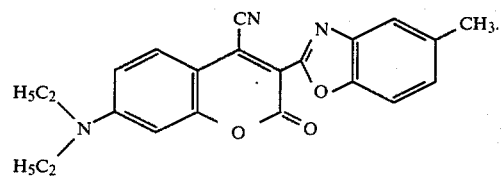

It dyes polyester fibres in fluorescent red shades having good overall fastness properties.

If there are used, instead of the aforementioned starting products, the two compounds of the formulae

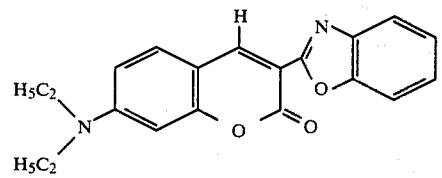

and

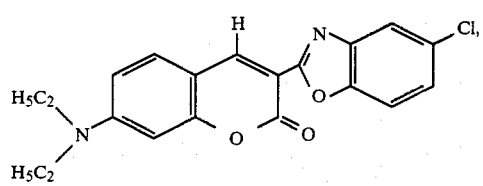

the procedure otherwise being as described, there are likewise obtained the corresponding 4-cyano compounds of the m.p.: 200°–203° respectively m.p.: 228°–229° which dye polyester in similarly fluorescent red shades.

EXAMPLE 3

150 g of th dye of the formula

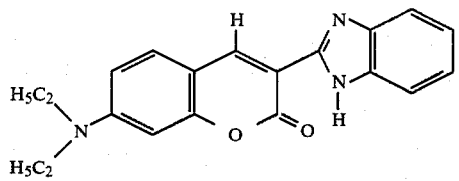

is suspended in 2.25 liters of dimethyl formamide, and 147 ml of 30% aqueous sodium cyanide solution is added. The mixture is stirred for 1 hour at 43°, and then oxidised at 8°–10° by the dropwise addition of 25.4 ml of bromine within 2 hours. After being stirred for 2 hours at 0°–10°, the mixture is filtered with suction, and the residue is washed with 100 ml of dimethyl formamide, and subsequently with water until free from salt. The yield after drying is 110 g of a dark-brown crystalline powder having a melting point of 265°–270°. The dye can be purified from unreacted starting product by recrystallisation from the 17-fold amount of chlorobenzene to yield 77 g of a black-lustrous powder with a melting point of 273°–277°. The formed dye corresponds to the formula

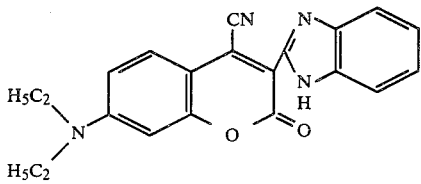

and dyes polyester fibres in red fluorescent shades.

EXAMPLE 4

1.45 g of the dye of the formula

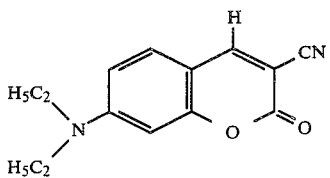

is suspended in 15 ml of dimethyl formamide, and 0.86 ml of 30% aqueous sodium cyanide solution is added. A virtually colourless solution has formed after about one hour, 10 ml of glacial acetic acid and 2.7 g of lead tetraacetate are added, and immediately an orange-red suspension is formed. This is stirred for a few hours and subsequently filtered, and the residue is washed free from salt with water. The yield obtained is 1.2 g of the dye of the formula

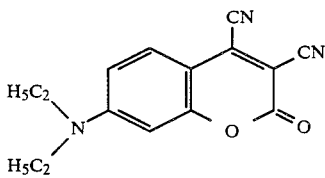

melting point: 210°–214°.

The dye is suitable for transfer printing, and on polyester fabrics are obtained orange printings and on polyacrylonitrile fabrics red printings, all having good overall fastness properties.

EXAMPLE 5

10.8 g of the dye of the formula

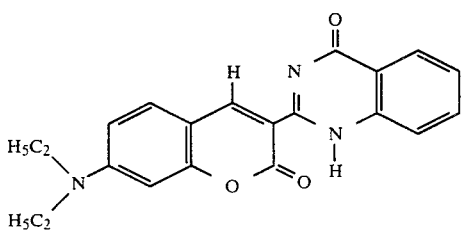

is suspended in 80 ml of dimethyl formamide, and the suspension is treated with 9.8 ml of 30% aqueous sodium cyanide solution and then with 1.54 ml of bromine, as described in Example 1. Corresponding further processing of the reaction mixture yields 5.9 g of the dye of the formula

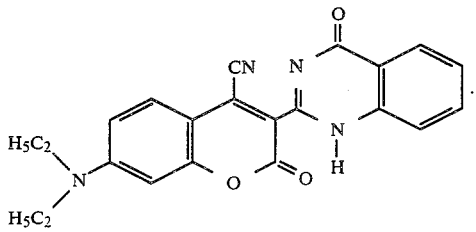

By recrystallisation from chlorobenzene is then obtained a dye having a melting point of 275°–278°. It dyes polyester fibres in bluish-red shades having good overall fastness properties.

EXAMPLE 6

1.9 g of the dye of the formula

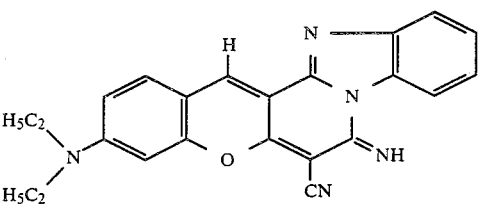

is suspended in 38 ml of dimethyl formamide, and 1.7 ml of 30% sodium cyanide solution is added. The mixture is filtered after one hour, and to the filtrate is added 2.6 g of lead tetraacetate. There is also added 5 ml of glacial acetic acid, and the mixture is stirred for 2 hours. The intense violet suspension is filtered, and the residue is washed with a small amount of dimethyl formamide, and then with water until free from salt. The yield after drying is 1 g of a dark powder having a melting point of 289°–291°. This dye dyes polyester in blue shades and corresponds probably to the formula

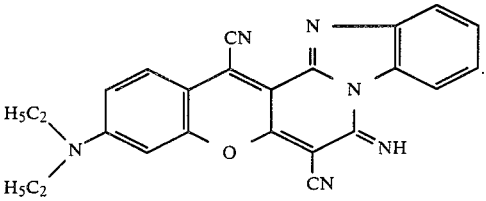

EXAMPLE 7

88.5 g of the compound

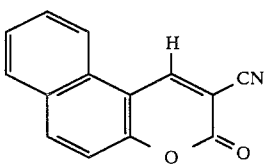

(produced by condensation of 2-hydroxy-naphthaldehyde-(—1) with ethyl cyanoacetate) is suspended in 560 ml of dimethyl formamide; there is then added 114 ml of a 30% aqueous NaCN solution, and the mixture is stirred for one hour at room temperature, in the course of which is formed a brownish-yellow solution. This is cooled to 0°-8° and within 85 minutes is added dropwise 24.6 ml of bromine; there results an orange-red suspension, which is stirred for one further hour at room temperature. It is filtered and the residue is then washed with 10 ml of dimethyl formamide. The press cake is subsequently washed free from salt with water and dried. The yield is 43 g of a brown powder having a melting point of 227°-229°. It is possible to recover from the mother liquor, by precipitation with water, a further 9 g of product. The dye has the following structure

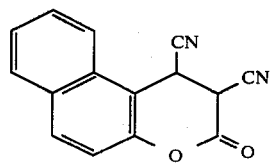

and are excellently suitable for printing polyester materials by the transfer printing method. Strong greenish-yellow printings having a pronounced fluorencence and good fastness to light are obtained.

EXAMPLE 8

2.85 ml of a 30% aqueous sodium cyanide solution is added to 3.6 g of the compound of the formula

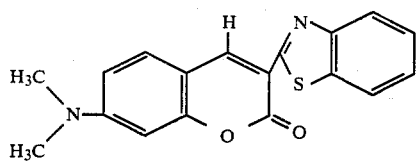

in 21 ml of dimethyl formamide. After 1½ hours' stirring at room temperature, the mixture is filtered until clear, and to the filtrate are added 5.2 g of lead tetraacetate (about 85%) and 2 ml of glacial acetic acid. The reddish-brown suspension is filtered after 10 minutes, and the residue is well washed firstly with methanol and then with water to thus obtain 1.8 g of the dye of the formula

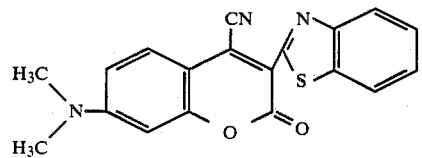

m.p. 240°-242° with which polyester materials can be dyed in fluorescent red shades.

EXAMPLE 9

1.2 g of the compound of the formula

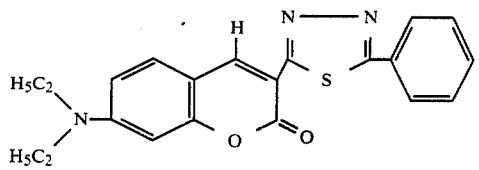

is suspended in 12 ml of dimethyl formamide, and at room temperature is added 0.86 ml of a 30% aqueous NaCN solution. Stirring is maintained for one hour at room temperature; the orange solution is then cooled to 0°-5°, and 1.6 g of lead tetraacetate is added. Stirring is continued for 10 minutes, and the red suspension is subsequently filtered off, and the residue is washed with ethanol and then with water and dried to yield 1 g of the dye of the formula

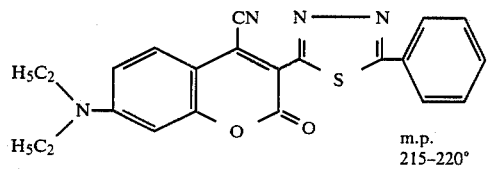

m.p. 215-220° which dyes polyester materials in fluorescent bluish-red shades having good overall fastness properties.

EXAMPLE 10

1.0 g of the compound of the formula

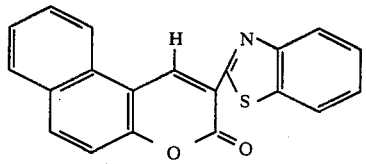

is suspended in 10 ml of dimethyl formamide, and 0.86 ml of a 30% aqueous NaCN solution is added. The orange-coloured solution is cooled to about 5°, and 0.8 g of dibenzoyl peroxide is added. Stirring is continued for one further hour, and the orange suspension is filtered off. The residue is washed with H₂O and dried. The yield is 0.3 g of the dye of the formula

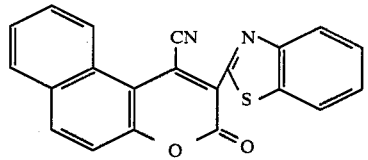

m.p. 214°-218°. From the mother liquor can be recovered, by precipitation with water, a further 0.6 g of the dye. The dye can be applied both from an aqueous bath and in the transfer printing process to polyester materials to produce thereon a brilliant yellow shade.

EXAMPLE 11

2.3 g of the compound of the formula

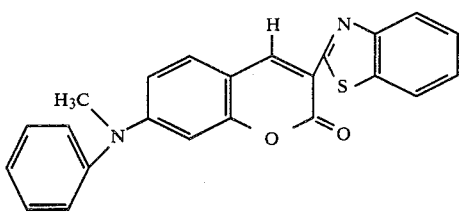

is suspended in 15 ml of dimethyl formamide, and at room temperature is added 1.7 ml of a 30% NaCN solution. From the yellow suspension is formed in a short space of time a red solution; this is stirred for about two hours and then cooled to 0°–10°, whereupon 0.33 ml of bromine is added. There is immediately formed a brown suspension, which is stirred for a further 15 minutes and then filtered. The residue is washed firstly with a small amount of methanol, and subsequently with a large amount of water and finally dried. The yield is 1.9 g of a brown catalyst powder having a melting point of 243°–250°. The dye corresponds to the formula

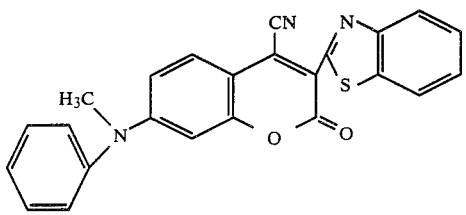

and is excellently suitable for dyeing polyester materials in brilliant red shades.

DYEING INSTRUCTION 1

1 part of the dye obtained according to Example 1 is ground wet with 2 parts of a 50% aqueous solution of the sodium salt of dinaphthylmethanedisulfonic acid, and dried.

This dye preparation is stirred with 40 parts of a 10% aqueous solution of the sodium salt of N-benzyl-$\mu$-hepta-decylbenzimidazoledisulfonic acid, and 4 parts of a 40% acetic acid solution are added. From this mixture is prepared, by dilution with water, a dye bath of 4000 parts.

Into this bath at 50° C. are introduced 100 parts of a cleaned polyester fibre material; the temperature is raised within half an hour to 120° to 130°, and the material is dyed at this temperature for one hour in a closed vessel. The material is subsequent well rinsed. There is obtained in this manner a full red fluorescent dyeing having excellent fastness to light and to sublimation.

DYEING INSTRUCTION 2

25 parts of the dye according to Example 1, which has previously been finely ground, are mixed with 550 parts of an 8% aqueous thickening from modified locust bean flour, 50 parts of a 10% solution of the sodium salt of m-nitrobenzenesulfonic acid, 10 parts of a mixture of potassium oleate and pine oil, and the amount is made up with water to 1000 parts. With the aid of a high-speed stirrer, the mixture is stirred to obtain a complete dispersion of the dye, and this paste is subsequently used to print polyethylene terephthalate. After printing, the fabric is dried, and steamed for 20 minutes at 1½ atm. (excess pressure); it is then rinsed for 10 minutes with cold water, soaped twice hot with the addition of a small amount of hydrosulfite, subsequently rinsed cold and finally dried. The result is a fast red printing.

DYEING INSTRUCTION 3

20 parts of the dye obtained according to Example 1 are ground with 140 parts of water containing 40 parts of the sodium salt of dinapthylmethanedisulfonic acid.

There is then prepared a padding liquor from 200 parts of the above dye preparation, 100 parts of carboxymethyl cellulose (4% aqueous solution) and 700 parts of water, by stirring the above described dye preparation, by means of a high-speed stirrer, into the prediluted thickening, and subsequently adjusting the pH value of the mixture to 6 with 80% acetic acid. A fabric made of polyester fibres is padded in this liquor at 30° with a squeezing effect of 60%, and the fabric is subsequently dried at 70° to 80°. The fabric is then heated on a clamping frame for 60 seconds at 210°, and then washed hot and afterwards thoroughly rinsed with cold water. The result is a deeply coloured fluorescent red-dyed fabric. The dyeing has good fastness properties.

DYEING INSTRUCTION 4

(a) 5 parts of the dye obtained according to Example 4, 6.5 parts of ethyl cellulose and 88.5 parts of ethanol are ground in a ball mill for 2 hours with cooling, and simultaneously homogenised. The grinding medium is then removed to leave an ink ready for printing.

(b) The printing ink obtained is printed onto a smooth parchment paper over the whole surface in a wet-film thickness of 24$\mu$, and subsequently dried. In this manner is obtained an intermediate carrier paper suitable for the transfer printing process.

(c) Onto the intermediate carrier pretreated in this way is placed a polyacrylonitrile fabric, and this is brought into contact with the treated side of the intermediate carrier, whereupon, by means of a heating plate, the intermediate carrier is pressed on and heated, from the untreated side, for 30 seconds at 200°, whilst a second unheated isolated plate provides from the back side of the printing substrate a uniform counterpressure. The dyed fabric is then removed from the carrier.

There is obtained in this manner a brilliant, deeply coloured polyacrylonitrile fabric which is dyed scarlet and which has good fastness to wet processing and to light.

(d) An orange dyeing having good fastness properties is obtained by using a polyester fabric instead of the polyacrylonitrile fabric.

DYEING INSTRUCTION 5

(a) 75 parts of the dye according to Example 2, 50 parts of an anionic dispersing agent, for example a lignin sulfonate or a condensation product from naphthalenesulfonic acid and formaldehyde, and 100 parts of water are mixed together and the mixture is converted in a ball mill, by being ground for 10 hours, into a finely divided form. The resulting suspension containing about 30% of crude dye is storage-stable.

(b) The aqueous dispersion obtained according to (a) can be processed into a printing paste as follows: 50 to 200 parts are stirred to a paste with 400 parts of a 10% locust bean flour thickening and 550 to 400 parts of water.

(c) A paper is printed with this printing paste in the gravure printing process. If this paper is pressed for 15 to 60 seconds at 210° against a textile made from polyester fibres, there is obtained a fluorescent red printing having good fastness to wet processing and to light.
I claim:
1. A compound of the formula
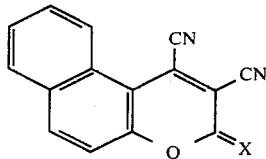
in which
X is =NH or =O.
2. A compound of claim 1, wherein X is =O.
* * * * *